United States Patent [19]

Decor

[11] 4,175,205

[45] Nov. 20, 1979

[54] PROCESS FOR THE PREPARATION OF VITAMIN A FROM SULPHONES

[75] Inventor: Jean-Pierre Decor, Thurins, France

[73] Assignee: Rhone-Poulenc Industries, Paris, France

[21] Appl. No.: 818,871

[22] Filed: Jul. 25, 1977

[30] Foreign Application Priority Data

Jul. 28, 1976 [FR] France .............................. 76 22992

[51] Int. Cl.² ........................ C07C 69/14; C07C 69/24
[52] U.S. Cl. ............................ 560/260; 260/607 AR; 568/824; 585/351
[58] Field of Search ............................ 560/249, 260; 260/607 AR, 617 A, 617 B, 666 C; 568/823, 824

[56] References Cited

U.S. PATENT DOCUMENTS

| | | |
|---|---|---|
| 3,803,252 | 4/1974 | Chabardes et al. .............. 260/666 C |
| 3,865,878 | 2/1975 | Chabardes et al. .................. 560/262 |
| 3,960,967 | 6/1976 | Olsen et al. .................... 260/607 AR |
| 4,048,234 | 9/1977 | Chabardes et al. ........... 260/607 AR |

OTHER PUBLICATIONS

Manchand, P. S., et al., "Synthesis of Vitamin A via Sulfones", Helvetica Chimica Acta, vol. 59, pp. 387–396, (March 1976).

*Primary Examiner*—James O. Thomas, Jr.
*Assistant Examiner*—Leah Hendriksen
*Attorney, Agent, or Firm*—Stevens, Davis, Miller & Mosher

[57] ABSTRACT

Vitamin A alcohol and its lower alkanoic esters are prepared by desulphonation of corresponding sulphones with a solid potassium alcoholate of a primary or secondary lower alcohol at 10° to 50° C. in an anhydrous liquid hydrocarbon.

6 Claims, No Drawings

PROCESS FOR THE PREPARATION OF VITAMIN A FROM SULPHONES

The present invention relates to the preparation of vitamin A from sulphones.

It is known, in particular from Belgian Pat. No. 794,872 (British Specification No. 1396622), that it is possible to prepare vitamin A by creating a double bond in the 11-12 position of the vitamin A unit by elimination of a substituent alkyl- or aryl-sulphonyl group. More precisely, it is known to prepare vitamin A derivatives of the formula:

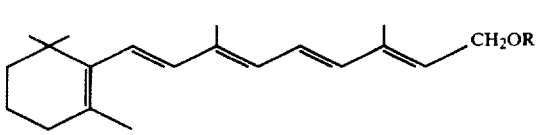

in which R represents hydrogen or $COR_1$, where $R_1$ is alkyl of 1 to 6 carbon atoms, by desulphonation of a sulphone of the formula:

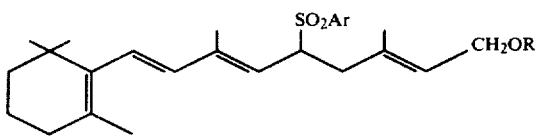

in which R is defined as above and Ar represents unsubstituted or substituted aryl. When the product is one in which R represents hydrogen, it may optionally be esterified.

Elimination of the arylsulphonyl group may be carried out by treating a sulphone of the formula (II) with an inorganic or organic basic agent in an organic solvent. However, the reaction only takes place with very small yields when it is effected in solvents with a high dipole moment or is very slow in solvents such as tetrahydrofuran or pyridine in the presence of potassium tert.-butylate. In order to obtain complete desulphonation it has been proposed to treat the compound of the formula (II), in which Ar is phenyl and R is $COCH_3$, with a alkali metal alcoholate in an alcoholic medium at a temperature of 80° C. for 4 to 16 hours [P. S. MANCHAND et al., Helv. Chim. Acta 59, 387 (1976)]; such operating conditions are, however, not very compatible with the low stability of the expected product.

It has now been found that it is possible to desulphonate a sulphone of formula (II) in excellent yield at a temperature of 10° to 50° C. using at least 3 molecular proportions per molecule of the said sulphone of a potassium alcoholate of a primary or secondary saturated, straight or branched chain aliphatic alcohol of 1 to 6 carbon atoms, in an anhydrous liquid hydrocarbon in which the said alcoholate is insoluble and is suspended in solid form. Under such conditions the degree of conversion of the sulphone of the formula (II) is quantitative and the yield of the product of the formula (I) can be as high as about 90%.

All hydrocarbons which are liquid at the temperature of the reaction and in which the potassium alcoholate, as defined above, is insoluble, are suitable. The hydrocarbon should also, of course, be such as not to react during the desulphonation. Preferably, the hydrocarbon used is a saturated straight or branched chain aliphatic hydrocarbon of 5 to 10 carbon atoms, a benzenoid hydrocarbon of 6 to 12 carbon atoms (such as benzene, toluene or xylene), or a cycloalkane hydrocarbon of 5 to 8 ring carbon atoms, which is unsubstituted or substituted by 1 to 3 straight or branched alkyl radicals of 1 to 4 carbon atoms each. More particularly, cyclohexane or hexane is used.

The quantity of the potassium alcoholate, as defined above, is not critical, the sole condition being that at least 3 mols of potassium alcoholate per mol of sulphone of the general formula (II) must be used; an excess is not harmful. Generally 3 to 5 mols of potassium alcoholate are used. Potassium methylate, ethylate or isopropylate is preferred.

Preferably, the sulphone of formula (II) is one in which Ar represents phenyl, nitrophenyl, or phenyl substituted by one or two halogens atoms or alkyl or alkoxy radicals of 1 to 4 carbon atoms each.

As in the known processes for the desulphonation of compounds of the formula (II), in which the symbol R represents a $COR_1$ radical as defined above, a partial saponification of the ester group occurs which leads to a mixture of products of the formula (I), in which R represents hydrogen and R represents $COR_1$. If desired, this mixture can be esterified by known methods to obtain a product of the general formula (I) in which the symbol R represents $COR_1$.

When a sulphone of the formula (II), in which R represents hydrogen, is desulphonated, since the corresponding product of the general formula (I) which is obtained is relatively unstable, it is generally preferred to convert it directly into a product of the formula (I) in which R represents $COR_1$, as defined above, by esterifying by any appropriate known method.

The products of the formula (II), in which R and Ar are defined as above, are known and can be prepared by the methods described in Belgian Pat. No. 794,872.

The following Examples illustrate the invention.

EXAMPLE 1

Ethanol (350 cc.) and the acetate sulphone (7.05 g.) ($15 \times 10^{-3}$ mol) of the formula:

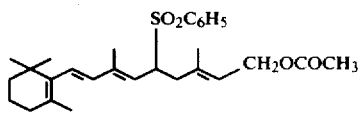

(prepared as described in Belgian Pat. No. 794,872) are charged, under argon, into a 1 liter flask which is kept in the absence of light. The mixture obtained is stirred. The sulphone does not completely dissolve. After stirring for 10 minutes a 1% aqueous solution of potassium hydroxide ($25 \times 10^{-3}$ mol; 140 cc.) is added and stirring is continued at about 25° C. The acetate sulphone progressively dissolves. After stirring for 45 minutes, it is verified by thin layer chromatography (eluant: hexane/tert.-butanol, 9:1 by volume) that the acetate sulphone has completely saponified to the alcohol sulphone. The ethanol is then distilled off under reduced pressure at a temperature of 45° C. The cloudy residual aqueous solution is extracted with diethyl ether (350 cc.). The extracts are washed with water (50 cc.) and then twice with saturated sodium chloride solution (a total of 80 cc.), and are then dried over sodium sulphate. A residue (6.7 g) is obtained by concentrating the extract under reduced pressure at about 25° C., finishing under a pressure of 0.1 mm Hg., for 2 hours 15 minutes. This residue is a pale yellow oil consisting of the alcohol sulphone of the formula:

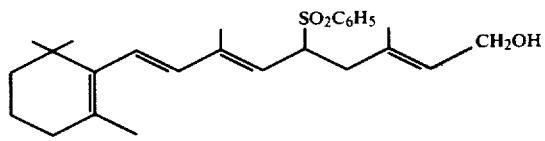

This alcohol sulphone is dissolved in anhydrous cyclohexane (200 cc.) at 28° C. Dry potassium methylate (3.685 g., $52 \times 10^{-3}$ mol) is added to the solution obtained, which is kept under argon, and the suspension is stirred. The liquid phase becomes pale mauve in colour whilst the temperature rises to 30° C. After stirring for one hour at 30° C., it is verified by thin layer chromatography that the alcohol sulphone has disappeared. The reaction mixture, which is coloured light chestnut, is cooled to 10° C. and then saturated sodium chloride solution (140 cc.) is added dropwise. The organic phase is separated and the aqueous phase is extracted twice with hexane (a total of 200 cc.). The different organic phases are combined, and washed 4 times with water (a total of 120 cc.) and then with saturated sodium chloride solution (30 cc.). Some drops of pyridine are added and the mixture is dried over sodium sulphate and concentrated under reduced pressure at about 25° C. until the volume of the residue is 150 cc.

Pyridine (1.985 g) and acetic anhydride (3.006 g) are added under argon, and in the absence of light, to the solution obtained, and the mixture is made up to 200 cc. by the addition of anhydrous hexane and heated to 40° C. for 4 hours 30 minutes. It is then verified by thin layer chromatography that all the alcohol has been converted into the acetate. The reaction mixture is cooled to 5° C. Hexane (70 cc.) is added and then water (110 cc.) is added over a period of 10 minutes, while the temperature is maintained at 5° C. The organic phase is separated, and washed successively with water (35 cc.) to which concentrated sulphuric acid (7 drops) has been added, with water (35 cc.) to which 10 N sodium hydroxide (14 drops) has been added, and finally with saturated sodium chloride solution (2×30 cc.) until neutral. After adding di-tert.-butylhydroxytoluene (0.21 g), which is used as a stabilising agent, drying over sodium sulphate and concentrating under reduced pressure at 35°–40° C., finishing under a pressure of 0.1 mm Hg., crude vitamin A (5.229 g) is obtained, the purity of which (determined by nuclear magnetic resonance, U.V. spectrography and high speed liquid chromatography) is 86% which corresponds to a yield of vitamin A units of 87% relative to the acetate sulphone starting material.

EXAMPLE 2

The acetate sulphone (0.94 g) ($2 \times 10^{-3}$ mol) of the formula:

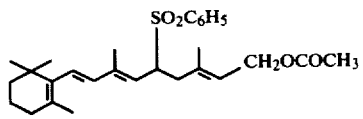

is added under argon to anhydrous hexane (20 cc.) maintained at 28° C. and the mixture is stirred briskly in order to disperse the acetate sulphone thoroughly. Potassium isopropylate (0.7 g, $7 \times 10^{-3}$ mol) is then added all at once through a wide-necked funnel and the funnel is rinsed with anhydrous hexane (5 cc.). The temperature of the mixture rises to 30°–31° C. and then falls again to 28° C. After stirring for 40 minutes, it is verified by thin layer chromatography that the desulphonation is complete. Ethyl acetate (20 cc.) is then added and the mixture is heated at 40° C. for 10 minutes. After cooling to about 25° C., the reaction mixture is poured into a mixture of iced water (200 cc.) and diethyl ether (100 cc.). The organic phase is separated, washed 3 times with water (a total of 150 cc.), dried over sodium sulphate, stabilised by the addition of di-tert.-butylhydroxyanisole (9.3 mg) and di-tert.-butylhydroxytoluene (18.6 mg), and concentrated under reduced pressure at about 25° C. A residue (0.6747 g of an orange-coloured oil) is thus obtained which is determined (by nuclear magnetic resonance, UV spectrography and high speed liquid chromatography) to contain 87% of vitamin A units.

EXAMPLE 3

The acetate sulphone (0.94 g) ($2 \times 10^{-3}$ mol) of the formula:

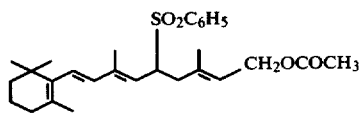

with an all trans structure, ethanol (45 cc.) and a 1% aqueous solution of potassium hydroxide ($3.57 \times 10^{-3}$ mol; 20 cc.) are charged, under argon, into a 100 cc. flask kept in the absence of light. The reaction mixture is stirred at about 25° C. for 45 minutes and the ethanol is then distilled off under reduced pressure at a temperature below 45° C. Water (50 cc.) is added to the residual mixture which is extracted successively with diethyl ether (50 cc. and then 3×25 cc.). The ether extracts are combined, washed with water and then with saturated sodium chloride solution, and dried over sodium sulphate. A residue weighing 0.856 g is obtained by concentrating under reduced pressure, which residue consists of the alcohol sulphone of the formula:

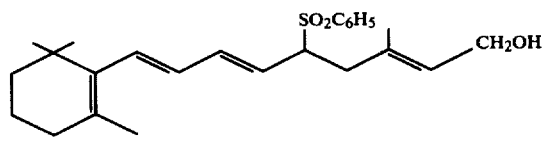

with an all-trans structure.

This alcohol sulphone is dissolved in cyclohexane (25 cc.) which has been distilled over $P_2O_5$. Potassium isopropylate (0.7 g) ($7 \times 10^{-3}$ mol) is added to the solution obtained. After having kept the mixture at 30° C. for 40 minutes with stirring, it is verified by chromatography that the desulphonation is complete. The mixture is cooled to 20° C. and then saturated sodium chloride solution (20 cc.) is added dropwise thereto and the mixture is extracted with hexane (45 cc.). The hexane extracts are washed 3 times with salt water (pH about 7, a total of 30 cc.) and pyridine (one drop) is added thereto. After drying over sodium sulphate and concentrating under reduced pressure, an oily residue weighing 0.595 g is obtained which is determined (by high speed liquid chromatography and UV spectrography) to contain 79% of vitamin A alcohol, corresponding to a yield of 81.9% based on the acetate sulphone starting material.

I claim:

1. In a process for the preparation of a vitamin A derivative of the formula:

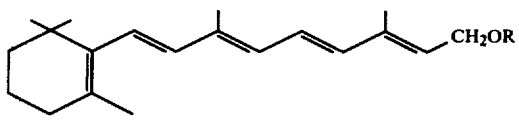

in which R represents hydrogen or COR$_1$, where R$_1$ is alkyl of 1 to 6 carbon atoms, by desulphonation of a sulphone of the formula:

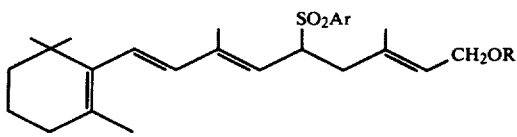

in which R is defined as above and Ar represents unsubstituted or substituted aryl, the improvement which consists in carrying out the desulphonation at a temperature of 10° to 50° C. using at least 3 molecular proportions per molecule of the said sulphone of a potassium alcoholate of a primary or secondary, saturated, straight chain or branched chain aliphatic alcohol of 1 to 6 carbon atoms, in an anhydrous liquid hydrocarbon in which the said alcoholate is insoluble and is suspended in solid form.

2. The improvement according to claim 1, in which the liquid hydrocarbon is a saturated straight or branched chain aliphatic hydrocarbon of 5 to 10 carbon atoms, a benzenoid hydrocarbon of 6 to 12 carbon atoms, or a cycloalkane hydrocarbon of 5 to 8 ring carbon atoms, which is unsubstituted or substituted by 1 to 3 straight or branched alkyl radicals of 1 to 4 carbon atoms each.

3. The improvement according to claim 2, in which the hydrocarbon is cyclohexane or hexane.

4. The improvement according to claim 1, in which Ar represents phenyl, nitrophenyl or phenyl substituted by one or two halogen atoms or alkyl or alkoxy radicals of 1 to 4 carbon atoms each.

5. The improvement according to claim 1, in which from 3 to 5 mols of the potassium alcoholate are used.

6. The improvement according to claim 5, in which the potassium alcoholate is potassium methylate, ethylate or isopropylate.

* * * * *